US00PP13795P39

(12) United States Plant Patent
Pieters

(10) Patent No.: US PP13,795 P3
(45) Date of Patent: May 13, 2003

(54) CHRYSANTHEMUM PLANT NAMED 'GEDI ONE YLSAP'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,858

(22) Filed: Jun. 4, 2001

(65) Prior Publication Data

US 2002/0184687 P1 Dec. 5, 2002

(51) Int. Cl.[7] ..... A01H 5/00
(52) U.S. Cl. ..... Plt./289
(58) Field of Search ..... Plt./295, 286, 287, Plt./289

(56) References Cited

U.S. PATENT DOCUMENTS

PP10,215 P 1/1998 Pieters ..... Plt./289

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a decorative type inflorescence, consistent flowering response to short days, blooming consistently after 49 days of short day length, free branching habit, yellow ray florets which resist fading with age, and a very uniform round growth habit.

1 Drawing Sheet

LATIN NAME

*Dendranthema morifolium*

VARIETY

'GEDI ONE YLSAP'

BACKGROUND OF THE INVENTION

Figure 1:
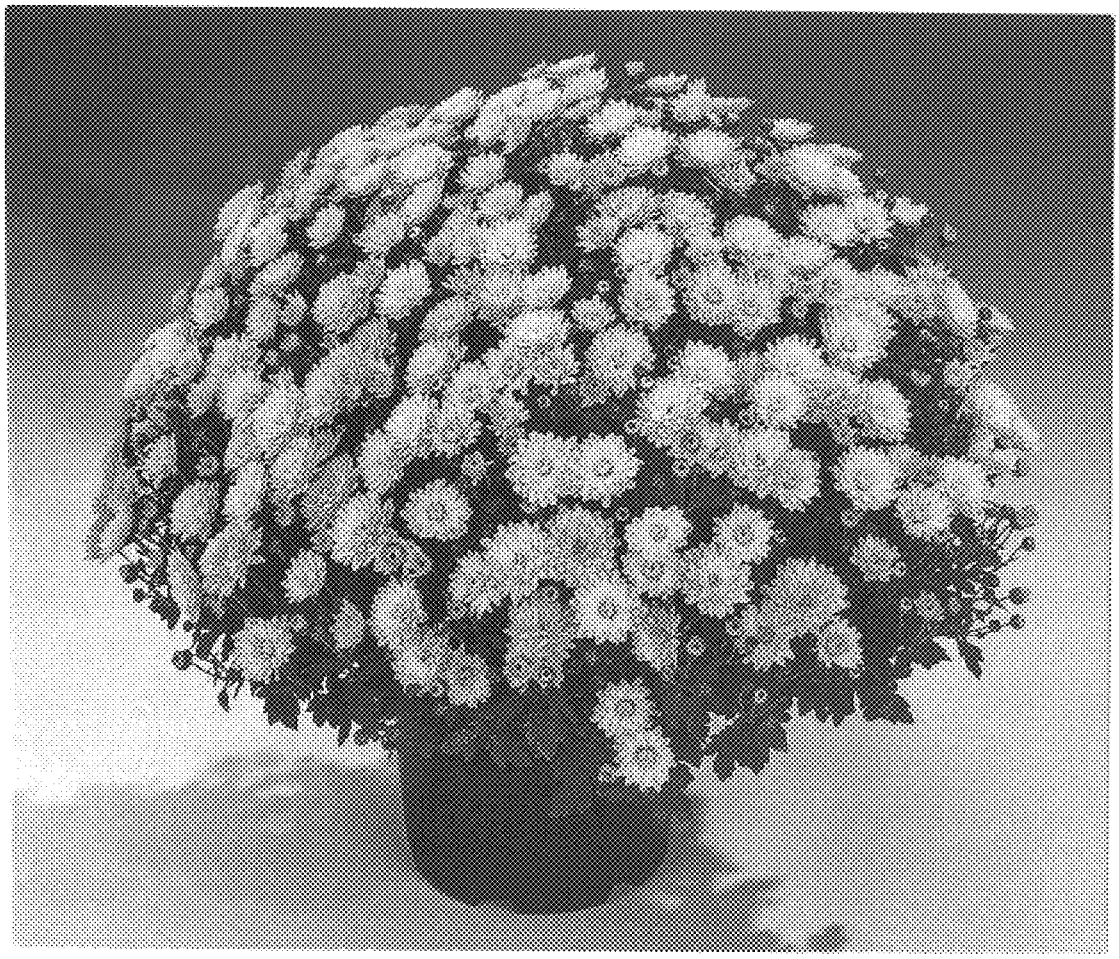

The present invention relates to a new and distinct cultivar of Chrysanthemum plant, herein after referred to by the cultivar name 'GEDI ONE YLSAP.'

This new cultivar was discovered in the inventor's field in Belgium in October 1997. The new cultivar was discovered as a naturally occurring mutation on a single branch of the parent variety, 'Sapiro', which is unpatented in the United States.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE YLSAP' has not been observed under all possible environmental conditions. The phenotype may vary somewhat with variations in environment such as temperature, daylength, and light intensity, without, however, any variance in genotype.

The following traits have been repeatedly observe and are determined to be the unique characteristics of 'GEDI ONE YLSAP.' These characteristics in combination distinguish 'GEDI ONE YLSAP' as a new and distinct Chrysanthemum:

1. Decorative type inflorescence;

2. Consistent flowering response to short days, blooming consistently after 49 days of short day length;
3. Free branching habit;
4. Yellow ray florets, resisting fading with age; and
5. Very uniform round growth habit.

Plants of the new cultivar are similar to plants of the parent cultivar, 'Sapiro,' in most horticultural characteristics, however plants of the new cultivar differed from plants of the cultivar 'Sapiro' in the number of blooms and the color of the ray florets. The new cultivar has slightly less blooms, as well as different colored ray florets, compared to the parent variety.

The new cultivar can be compared to the Chrysanthemum cultivar 'Dark Veria' (disclosed in U.S. Plant Pat. No. 10,215). However plants of the new Chrysanthemum differed from the plants of the cultivar 'Dark Veria' in the following characteristics:

1. New cultivar naturally blooms approximately 1 week later than 'Dark Veria;'
2. New cultivar is taller and wider than 'Dark Veria;'
3. New cultivar has a more round plant shape and greater branching than 'Dark Veria;' and
4. New cultivar has more blooms per flowering branch 'Dark Veria.'

BRIEF DESCRIPTION OF THE PHOTOGRAPHS

The photograph shows a plant of 'GEDI ONE YLSAP' grown in a 2 gallon container. One cutting was used in the pot, planted mid May and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000, 135 days from rooted cuttings. The growing conditions range from 60° to 65° F. at night to 70° to 85° F. during the day. Measurements and numerical values represent averages of typical flowering types.

Botanical classification: *Dendranthema morifolium* cultivar 'GEDI ONE YLSAP'.
Commercial classification: Garden-type Chrysanthemum
Parentage: Naturally occurring mutation on a single branch of the variety 'Sapiro'.

PROPAGATION

Time to rooting: 7 to 14 days at approximately 21° C.
Root description: Fine, fibrous.

PLANT

Growth habit: Mounding herbaceous perennial.
Height: Approximately 24 cm.
Growth rate: Moderate.
Plant spread: Approximately 26 cm.
Branching characteristics: Free Branching.
Length of lateral branches: Approximately 21 cm.
Number of leaves per lateral branch: About 24.
Stem color: Near 138A.

FOLIAGE

Leaf:
- *Arrangement.*—Alternate, single.
- *Average length.*—Approximately 6.2 cm.
- *Average width.*—Approximately 3.6 cm.
- *Shape of blade.*—Ovate.
- *Apex.*—Acuminate.
- *Base.*—Attenuate.
- *Attachment.*—Stalked.
- *Margin.*—Pinnately lobed and toothed.
- *Texture of top surface.*—Lightly pubescent.
- *Texture of bottom surface.*—Lightly pubescent.
- *Color.*—Young foliage upper side: Near 137A young foliage under side: Near 137B mature foliage upper side: Near 137A mature foliage under side: Near 137B venation upper side: Near 138C venation under side: Near 137C.

Petiole:
- *Average length.*—Approximately 2.1 cm.
- *Color.*—138A.
- *Diameter.*—2 mm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the first two weeks of October.
- *Number of inflorescences per stem.*—Approximately 15.
- *Inflorescence diameter.*—Approximately 5.2 cm.
- *Inflorescence depth.*—2.0 cm.
- *Inflorescence longevity on plant.*—Approximately 22–26 days.
- *Persistence.*—Persistent.

Ray florets:
- *Appearance.*—Matte.
- *Texture.*—Smooth.
- *Average number per flower.*—200.
- *Shape.*—Oblanceolate.
- *Margin.*—Entire.
- *Apex.*—Obtuse.
- *Length.*—Approximately 3.1 cm.
- *Width.*—Approximately 0.8 cm.
- *Color.*—Upper surface at first opening: Near 15C upper surface at maturity: Near 17D upper surface at fading: Near 15D under surface at first opening: Near 15B under surface at maturity: Near 17D under surface at fading: Near 15D.

Disc florets:
- *Appearance.*—Shiny.
- *Texture.*—Smooth.
- *Average number per flower.*—Approximately 60.
- *Shape.*—Cylindric.
- *Apex.*—Obtuse.
- *Average length.*—Approximately 1 cm.
- *Average width.*—Approximately 0.2 cm.
- *Color.*—At first opening: Near 2A at maturity: Near 21A at fading: Near 17D.

Peduncle:
- *Length.*—At terminal end (shortest): Approximately 5 cm at lateral end (longest): Approximately 9 cm.
- *Strength.*—Moderate.
- *Color.*—Near 137C.
- *Habit.*—Erect.
- *Surface texture.*—Lightly pubescent.

Inflorescence bud:
- *Length.*—Approximately 1 cm.
- *Diameter.*—Approximately 1 cm.
- *Form.*—Globular.
- *Color.*—Near 15A.

Phyllaries:
- *Appearance.*—Matte.
- *Texture.*—Lightly pubescent.
- *Number.*—Approximately 40 to 50.
- *Shape.*—Ovate.
- *Margin.*—Entire.
- *Apex.*—Acute.
- *Diameter.*—0.3 cm.
- *Length.*—0.5 cm.
- *Color.*—Upper side: Near 137A under side: Near 137A.

REPRODUCTIVE ORGANS

Ray florets:
- *Number of pistils per flower.*—1.
- *Stigma shape.*—2 branched.
- *Stigma color.*—Near 15B.
- *Style color.*—Near 15D.
- *Style length.*—0.6 cm.
- *Stamens*—Absent.

Disc florets:
- *Number of pistils per flower.*—1.
- *Stigma shape.*—Cylindric.
- *Style length.*—0.5 cm.
- *Number of stamens per flower.*—Approximately 5.
- *Anther shape.*—Tubular.

*Anther color.*—Near 15A.
*Pollen color.*—Near 16B.

OTHER CHARACTERISTICS

Seed production: Commercially, this plant is not used or observed in a stage wherein seeds would be produced. Therefore, seed production has not been observed to date.

Disease resistance: Neither resistance nor susceptibility to diseases and pests have been observed to date in this cultivar.

What is claimed is:

1. A new and distinct variety of Chrysanthemum plant named 'GEDI ONE YLSAP' as herein illustrated and described.

* * * * *